(12) United States Patent
Von Drasek (10) Patent No.: US 7,244,936 B2
(45) Date of Patent: Jul. 17, 2007

(54) CHEMICAL SPECIES DETECTION INCLUDING A MULTISECTION LASER FOR IMPROVED PROCESS MONITORING

(75) Inventor: William A. Von Drasek, Oak Forest, IL (US)

(73) Assignee: American Air Liquide, Inc., Houston, TX (US)

( * ) Notice: Subject to any disclaimer, the term of this patent is extended or adjusted under 35 U.S.C. 154(b) by 24 days.

(21) Appl. No.: 11/211,073

(22) Filed: Aug. 25, 2005

(65) Prior Publication Data

US 2006/0124852 A1   Jun. 15, 2006

Related U.S. Application Data

(60) Provisional application No. 60/634,936, filed on Dec. 10, 2004.

(51) Int. Cl.
*G01J 5/02* (2006.01)
(52) U.S. Cl. .................................. 250/339.13
(58) Field of Classification Search ............ 250/339.13
See application file for complete search history.

(56) References Cited

U.S. PATENT DOCUMENTS

| | | | |
|---|---|---|---|
| 5,748,325 A * | 5/1998 | Tulip | 356/437 |
| 5,813,767 A | 9/1998 | Calabro' et al. | |
| 5,832,842 A | 11/1998 | Frontini et al. | |
| 6,862,301 B2 | 3/2005 | Cox | |
| 2002/0151126 A1 * | 10/2002 | Jacquet | 438/200 |
| 2003/0132389 A1 | 7/2003 | Von Drasek et al. | |
| 2006/0133714 A1 * | 6/2006 | Sappey et al. | 385/13 |

FOREIGN PATENT DOCUMENTS

WO       03069742 A    8/2003

OTHER PUBLICATIONS

Rothman, L.S., et al., "The HITRAN Molecular Database: Editions of 1991 and 1992," J. Quant. Spectrosc. Radiat. Transfer, 48, 469-507.
Ebert, V., et al., "Simultaneous Diode: Laser-Based In situ Detection of Multiple Species and Temperature in Gas-Fired Power Plant," Proceedings of the Combustion Institute, vol. 28, pp. 423-430, 2000.
Furlong, E.R., et al., "Diode-Laser Sensors for Real-Time Control of Temperature and $H_2O$ in Pulsed Combustion Systems," 34$^{th}$ AIAA/ASME/SAE/ASEE Joint Propulsion Conference, AIAA-98-3949, 1998.

(Continued)

*Primary Examiner*—David Porta
*Assistant Examiner*—Marcus H Taningco
(74) *Attorney, Agent, or Firm*—Elwood L. Haynes; Christopher J. Cronin (57) ABSTRACT

A gas species monitoring system includes a laser system, where the laser system includes a multisection DBR laser, and a plurality of measurement points disposed at different locations within the system. The laser system is configured to selectively deliver a laser beam from the multisection DBR laser to each measurement point within the system to determine a concentration of at least one gas species at each measurement point. A chemical detection grid is aligned with the ITU-GRID to facilitate use of a multisection DRB laser that operates within one or more of the defined bands of the ITU-GRID.

2 Claims, 4 Drawing Sheets

OTHER PUBLICATIONS

Ebert, V., et al., "Simultaneous Laser-Based In situ Detection of Oxygen and Water in a Waste Incinerator for Active Combustion Control Purposes," Proceedings of the Twenty-Seventh Symposium (International) on Combustion, The Combustion Institute, vol. 27, pp. 1301-1308, 1998.

International Search Report dated Mar. 20, 2006.

Upschulte, Bernard, et al., "In Situ, Multi-Species Combustion Sensor Using a Multi-Section Diode Laser", AIAA Paper 98-0402, *36th Aerospace Sciences Meeting & Exhibit*, Jan. 12-15, 1998, Reno, NV.

Von Drasek, William et al., "Tunable Diode laser Sensor for Multiple Species Monitoring in Harsh Atmospheres," *SPIE International Symposium on Optical Technologies for Industrial, Environmental, and Biological Sensing*, Providence, Rhode Island, Oct. 28-30, 2003.

\* cited by examiner

CHEMICAL SPECIES DETECTION INCLUDING A MULTISECTION LASER FOR IMPROVED PROCESS MONITORING

CROSS-REFERENCE TO RELATED APPLICATIONS

This application claims priority from U.S. Provisional Patent Application Ser. No. 60/634,936, entitled "Chemical Species Detection Grid for Improved Process Monitoring and for Distributed Gas Monitoring", and filed Dec. 10, 2004. The disclosure of this provisional patent application is incorporated herein by reference in its entirety.

BACKGROUND OF INVENTION

1. Field of Invention

The present invention pertains to monitoring gas species in various gas streams and at varying temperature and other process locations using a multisection laser.

2. Related Art

The use of near-infrared diode lasers for process gas monitoring is highly advantageous due at least in part to a number of chemical species of interest (e.g., CO, $CO_2$, $H_2O$, $NO_2$, etc.) that can be detected with such lasers. In addition, diode laser devices developed for use in telecommunication applications can be readily adaptable for gas detection applications. For example, many of the device requirements for telecommunication applications, such as narrow line width, rapid tuning capability, etc., parallel the requirements for gas detection. Though semiconductor lasers in principle can be manufactured at any wavelength in the NIR region defined by the matrix material, the availability of lasers at specific wavelengths is limited to either custom made lasers or matching telecommunication laser wavelengths with desired absorption features of interest.

The narrow line width and tunability by temperature and current injection are key advantages in using diode laser devices for gas species detection. These features provide the necessary specificity to detect spectral absorption features for a particular chemical species without interferences from surrounding species. However, a main disadvantage associated with applying typical diode lasers for gas monitoring (e.g., a distributed feedback or DFB laser) is the limited tuning range (about 1-3 $cm^{-1}$) for current injection, which in turn limits the spectral information detectable by a single device. A larger tuning range is possible with temperature control, but this negatively impacts the response time of the measurement. Therefore, in multiple species or multiple absorption line monitoring for control applications, several lasers are typically applied with each laser dedicated to the absorption line or lines accessible by the device.

Species concentration monitoring is performed by propagating a tunable laser beam from a laser through the gas matrix of interest which can be in-situ or provided from an extracted sample. In the case of in-situ monitoring, the process gas temperature must be known to accurately determine the species concentration. The process gas temperature is necessary, because the resultant absorption signal that is recorded is dependent on temperature through the absorption coefficient that appears in the Beer-Lambert law as the product of the line strength and line shape functions. The Beer-Lambert relation describes the resulting absorption of the laser radiation along the measurement path for a single species as follows:

$$I_v = I_{v,o} e^{[-S(T)g(v-v_o)Nl]} \quad (1)$$

where $I_v$ is the laser intensity at frequency v measured after the beam has propagated across a path l with N absorbing molecules per volume. The incident laser intensity is $I_{v,o}$ and is referred to as the reference. The amount of laser radiation attenuated is determined by the temperature dependent line strength S(T) and the lineshape function $g(v-v_o)$. Inversion of the above equation relates the number density N to the measured laser intensities and known linestrength and pathlength as follows:

$$N = \frac{1}{S(T)l} \cdot \int \ln\left(\frac{I_{vo}}{I_v}\right) dv \quad (2)$$

With the exception of S(T) in the above equation, the parameters are either measured or known. If the process temperature is relatively constant, then S(T) can be considered constant from either calibration measurements or from validated database values, e.g., values obtained from a HITRAN-HITEMP database.

Direct application of the Beer-Lambert law applies for measurements that monitor the direct absorption of the laser radiation passed through the absorbing medium. Other techniques apply wavelength modulation spectroscopy (WM) or Frequency modulation (FM) spectroscopy to reduce the inherent noise of the laser. In using WM or FM spectroscopy, the recorded spectral data can be either modeled or compared with a library of spectra to obtain the best fit for a given concentration and temperature. In either application (i.e., direct absorption or a modulation technique), processes that undergo temperature variations require a mechanism for obtaining the gas temperature to determine the correct value of the linestrength. In slow temperature varying processes, temperature information can be obtained from the refractory wall temperature by either a thermocouple or optical pyrometer measurements in particle free systems. However, in dynamic processes, the response time of wall temperatures is too slow for an accurate determination of S(T). Therefore, an alternative mechanism for obtaining the temperature is needed for real-time process monitoring.

In U.S. Pat. No. 5,813,767, a multiple laser system is described for waste incineration monitoring. In addition, this patent document describes a method of determining the temperature from the Gaussian component of the recorded spectral line based upon an identification of the Doppler contribution, which depends solely on the temperature. This method is limited in use since extremely high quality data is required to obtain accurate results. For applications on industrial processes that experience high particle densities, temperature gradients, mechanical vibration, rapid variations in temperature and gas composition, and high radiation loads from the process, all of these factors can contribute at different degrees to degrade the quality of the spectrum, thus introducing errors in the results.

In addition, the tuning range of distributed feedback (DFB) lasers limits the level of spectral information that can be monitored by a single device. Extension of the tuning range over several nanometers can be obtained by varying the device temperature, but this method sacrifices the speed at which multiple spectral regions can be monitored due to the time required for the laser to become thermally stable. Alternatively, external cavity lasers such as those commercially available from New Focus (a Division of Bookham, Inc., San Jose, Calif.) operate with a broad tuning range (e.g., a tuning range of 1520-1570 nm with tuning speed of 10 nm/s), but with a sacrifice in speed.

While a single DFB laser system can be used to monitor two or more gas species of interest in a composition, such a single laser system will be limited to set temperature conditions. For example, in a CO monitoring system using a DFB laser near 1560 cm$^{-1}$ for combustion process monitoring, the concentration of $H_2O$ within the composition must also be determined due to the interference that occurs between $H_2O$ peaks and CO peaks at a particular region along the absorption spectrum, since the concentration of a species is determined by measuring the absorption peaks corresponding with the species along the absorbance spectrum for a particular wavelength scan. The concentration of $H_2O$ must be determined to correct for such interference so as to determine an accurate CO concentration. Such correction becomes particularly important for CO concentrations of 1% or less (where the CO peaks are very tiny and possibly masked by $H_2O$ interference peaks). In this example, temperature sensitivity and the level of $H_2O$ peak interference decreases as temperatures approach 1090 K. However, for temperatures of 1090 K or greater, the temperature sensitivity becomes a major factor, thus limiting the accuracy of a single DFB laser for determination of CO concentrations.

In applications where multiple point monitoring is desired, the above-described limitations of the DFB laser restrict these monitoring applications to the conditions that match the diode laser-tuning window. For example, using a DFB laser for monitoring CO and $H_2O$ at a process location with a characteristic temperature of 1500 K and another point with a characteristic temperature of 800 K would not be feasible. To monitor these two locations would require a minimum of two DFB lasers to capture the spectral data at each location with the desired sensitivity. As the number of measurement points or locations or variations in characteristic measurement conditions (e.g., large fluctuations in temperature) increases for a particular application, the number of DFB lasers required also increases.

Therefore, applications requiring multiple species monitoring, as required in high temperature processes where the temperature is unknown or varies, typically require several DFB lasers to maintain a fast-response time and accuracy. An exemplary multiple species monitoring system is described in U.S. Pat. No. 5,832,842, which includes a plurality of lasers for monitoring the compositions of CO, $O_2$, $H_2O$ and HCl in combustion fumes from incineration plants so as to control the fume acidity. Other examples implementing multiple DFB lasers are described in Ebert et al., *"Simultaneous Diode-Laser-Based In situ Detection of Multiple Species and Temperature in Gas-Fried Power Plant"* Proceedings of the Combustion Institute, Vol. 28, pp. 423-430, 2000 (for monitoring species in a 1 GW gas-fired power plant) and Furlong et al., *"Diode-Laser Sensors for Real-Time Control of Temperature and $H_2O$ in Pulsed Combustion Systems,"* 34th *AIAA/ASME/SAE/ASEE Joint Propulsion Conference*, AIAA-98-3949, 1998 (for monitoring species in a pulsed waste incinerator).

In such multiple laser systems, the integration of multiple lasers into a system adds to the system complexity and cost by requiring additional wavelength discriminating mechanisms for the different laser wavelengths (e.g., additional supporting electronics, such as temperature and current controllers for each DFB laser in a multiple laser system as well as multiplexing equipment).

SUMMARY OF THE INVENTION

It is an object of the present invention to provide a laser-based gas detection system capable of detecting multiple gas species at varying temperatures and multiple measurement points or locations.

It is another object of the present invention to provide a laser-based gas detection system that is accurate, reliable and fast and further reduces system complexity and the number of lasers required to monitor a broad spectral range.

The aforesaid objects are achieved individually and/or in combination, and it is not intended that the present invention be construed as requiring two or more of the objects to be combined unless expressly required by the claims attached hereto.

In accordance with the present invention, a gas species detection system includes a gas species monitoring system includes a laser system, where the laser system includes a multisection DBR laser, and a plurality of measurement points disposed at different locations within the system. The laser system is configured to selectively deliver a laser beam from the multisection DBR laser to each measurement point within the system to determine a concentration of at least one gas species at each measurement point.

In accordance with another embodiment of the present invention, a method of monitoring one or more gas species at one or more measurement points comprises directing a laser beam from a multisection DBR laser to a first measurement point to facilitate a measurement of at least one gas species at the first measurement point, and directing a laser beam from the multisection DBR laser to a second measurement point to facilitate a measurement of at least one gas species at the second measurement point, where at least one of a temperature and a gas species differs at each of the first and second measurement points.

A chemical species detection grid is developed in accordance with the invention and matched with a multi-section DBR laser developed for DWDM applications. In particular, the chemical species detection grid is aligned with the ITU-GRID used by the telecommunication industry, which defines unique lines separated by 50 GHz. The conventional approach of using individual DFB lasers to access the same channels requires multiplexed and more complicated laser systems for multiple absorption line monitoring, since the DFB lasers are limited in wavelength tuning range. Implementation of a multi-section DBR laser developed for ITU-GRID communication applications into a gas species monitoring system allows for multiple absorption line detection using a single device, which thereby simplifies the overall gas sensor system architecture. This in turn allows improved monitoring capabilities with regard to measurement accuracy and flexibility. The added flexibility provides optimum absorption transition selection that extends the range of conditions (e.g., temperature and concentration) for process monitoring.

The above and still further objects, features and advantages of the present invention will become apparent upon consideration of the following detailed description of specific embodiments thereof, particularly when taken in conjunction with the accompanying drawing.

DESCRIPTION OF PREFERRED EMBODIMENTS

In accordance with the present invention, a multiple gas species monitoring system is provided that utilizes a single multisection laser, where the multisection laser monitors one or more gas species at two or more measurement points, stations or locations of a process. The system is effective at monitoring one or more of the same or different gas species at the different measurement points despite temperature variations between stations. In particular, the multisection laser is capable of monitoring gas species at two or more different measurement points, where the temperature at each measurement point can vary from measurement point to measurement point from ambient temperatures (e.g., about 20° C. or less) to about 3000° C. or greater. For example, depending upon a particular application, the multisection laser of the system can monitor at least two different measurement points that differ in temperature by at least about 100° C. In other applications, the multisection laser of the system can monitor two or more different measurement points that differ in temperature by at least about 200° C., at least about 300° C., at least about 400° C., at least about 500° C. and/or at least about 600° C. Exemplary gas species that can be monitored in the system include, without limitation, $H_2O$, HF, HI, HCN, $H_2S$, CO, $CO_2$, OH, alkyl species (e.g., $CH_4$), and $NH_3$.

In particular, the laser utilized in the system of the present invention is a multisection distributed Bragg reflector (DBR) laser that is designed for dense wavelength division multiplexing (DWDM) applications. A chemical species detection grid has also been developed and aligned with the International Telecommunication Union Grid (ITU-GRID), where the ITU-GRID defines bands of spectral lines or channels separated by 50 GHz. This allows the system to utilize a standard DBR laser that is commercially available and suitable for use in a known band of the ITU-GRID, thus avoiding the necessity for forming a customized laser. However, any suitable multisection DBR laser can be employed in accordance with the invention that is capable of scanning over a selected wavelength range to detect and monitor one or more gas species at one or more locations during system operation.

The multisection DBR laser can be combined with a fiber amplifier (e.g., an erbium doped fiber amplifier or EDFA), and a variable optical attenuation VOA system (e.g., as described in U.S. patent application Ser. No. 11/045,513, the disclosure of which is incorporated herein by reference in its entirety) to provide linear control for the output laser power being sent to the different measurement locations as well as a high level of accuracy in the gas species detection and concentration measurements over a range of wavelengths and output laser power values for the fiber amplifier.

In a preferred embodiment, the laser to be used in a gas species detection system is a modified version of any of the multisection DBR lasers commercially available from Agility Communication, Inc. (Santa Barbara, Calif.) and that can access all ITU-GRID channels in a particular band (e.g., the C-band, which corresponds with a wavelength range of about 1530 nm to about 1565 nm), with a separation of about 50 GHz per channel. These multisection DBR lasers are designed for DWDM applications and are capable of tuning to any of the channels within a particular band in 1 μs. In addition, these lasers have been modified for use in the gas species detection systems of the present invention such that they are capable of continuously sweeping the laser phase current to allow continuous wavelength scanning of about ±20 GHz around each ITU-GRID channel. Further, the compatibility of these multisection DBR lasers with standard EDFAs extends the range of applications of the lasers (e.g., in high particle density and high vibration processes) while ensuring reliability of gas species detection and concentration measurements.

A multisection DBR laser can be utilized in any gas species detection and monitoring system in accordance with the present invention, where the laser is capable of sweeping a laser signal in any of the defined ITU-GRID bands as set forth in Table 1:

TABLE 1

ITU-GRID bands

| Band | Band description | Wavelength Range (nm) |
| --- | --- | --- |
| O-band | Original | 1260–1360 |
| E-band | Extended | 1360–1460 |
| S-band | Short | 1460–1530 |
| C-band | Conventional | 1530–1565 |
| L-band | Long | 1565–1625 |
| U-band | Ultra-long | 1625–1675 |

As noted above, multisection DBR lasers are commercially available (e.g., from Agility Communication, Inc.) for a particular ITU-GRID band, thus allowing for implementation of such a laser in a gas species detection and monitoring system with relative ease. However, a multisection DBR laser can also be implemented in a gas species detection and monitoring system that is capable of scanning a laser beam or signal over wavelength ranges that cover and/or overlap two or more ITU-GRID bands as set forth in Table 1 above.

An exemplary listing of the wavelength or wavelengths at which a variety of gas species are detectable by laser absorption and that fall within an ITU-GRID band as described above is provided in Table 2 below. The detection conditions for the wavelength absorption data of Table 2 are based upon $1 \times 10^{-5}$ absorbance, 1 Hz bandwith, 1 meter pathlength and ambient temperatures, where the wavelength listed for each gas species is a marker or identification location for where the absorption transition range occurs for that gas species at the previously noted detection conditions. It is further noted that spectral data for a gas species of interest in a particular application and based upon temperature and other system conditions can be readily obtained for wavelengths corresponding with one or more of the previously identified ITU-GRID bands.

TABLE 2

Detectable Wavelength for Gas Species

| Species | Detection limit (ppb) | Wavelength (nm) |
| --- | --- | --- |
| Water | 60 | 1390 and 1500 |
| Carbon Dioxide | 3000 | 1625 |

TABLE 2-continued

Detectable Wavelength for Gas Species

| Species | Detection limit (ppb) | Wavelength (nm) |
|---|---|---|
| Carbon Monoxide | 30000 | 1570 |
| Methane | 600 | 1650 |
| Acetylene | 80 | 1520 |
| Hydrogen Fluoride | 10 | 1310 |
| Hydrogen Iodide | 2100 | 1540 |
| Hydrogen Cyanide | 290 | 1540 |
| Hydrogen Sulfide | 20000 | 1570 |
| Ammonia | 800 | 1500 |

In a system where one or more gas species of interest need to be monitored (e.g., CO and $H_2O$), a multisection DBR laser can be selected, in accordance with the present invention, that is capable of performing wavelength sweeps in the appropriate band or bands that correspond with the peak or optimum absorption transitions for these species of interest. In addition, when two or more gas species monitored at one or more locations within the system have absorption transitions that are situated in different bands (e.g., C-band and S-band), two or more multisection DBR lasers may be provided to monitor both species. Alternatively, a single multisection DBR laser can be provided that sweeps in a wavelength range that encompasses suitable portions of the different bands.

The extended tuning range capability of the multisection DBR laser allows selection of optimum absorption transitions for a number of gas species, which in turn extends the dynamic range of the laser for process monitoring. Thus, a single multisection DBR laser device can be implemented in a system for detection and monitoring of one or more gas species at multiple measurement points, stations or locations where the process monitoring conditions are very different. In particular, the single multisection DBR laser device of the invention can monitor multiple measurement points, where the temperature can vary from measurement point to measurement point from ambient temperatures (e.g., about 20° C. or less) to about 3000° C. or greater. This is in direct contrast to typical DFB lasers used for gas species monitoring, which are limited to operation in a small spectral window such that systems requiring multiple measurement points or monitoring locations to monitor different gas species and/or having large temperature fluctuations from measurement point to measurement point would further require multiple DFB lasers (e.g., 100 or more) to obtain accurate and reliable spectral data at the different measurement points.

Figure 1:
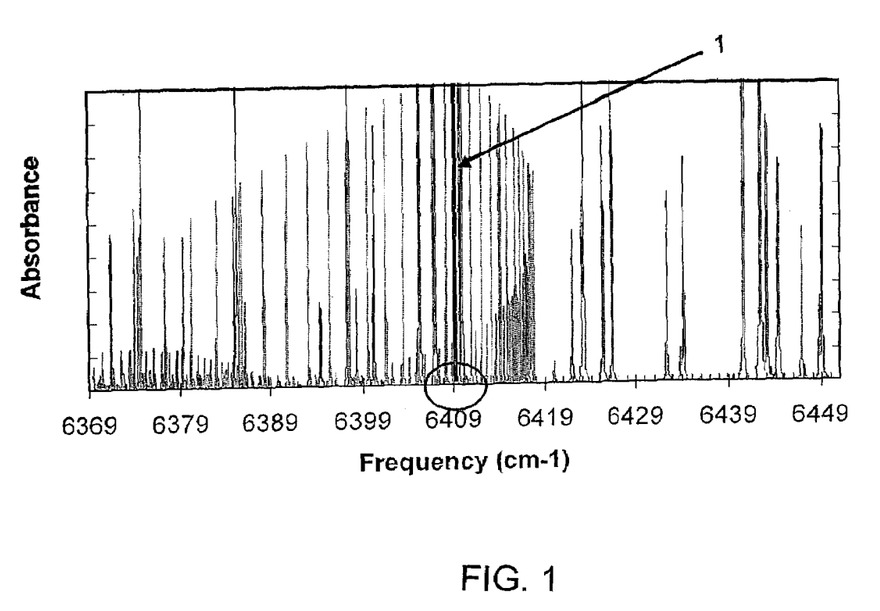
FIG. 1 is a plot of absorbance spectra of $H_2O$, CO and $CO_2$ at 1500 K as obtained from the HITRAN-HITEMP database.

To clearly show the limitations of DFB lasers and the advantages of utilizing a multisection DBR laser for gas species monitoring in accordance with the invention, spectra simulations were performed using the HITRAN-HITEMP database. Referring to FIG. 1, a spectral region of data is plotted where CO, $H_2O$ and $CO_2$ are present at a gas monitoring or sampling temperature of 1500 K. In particular, the $CO_2$ absorption spectral data includes peaks extending between 6389 $cm^{-1}$ and 6395 $cm^{-1}$, the CO absorption spectral data includes peaks extending between 6375 $cm^{-1}$ and 6419 $cm^{-1}$, while the $H_2O$ absorption spectral data includes peaks extending throughout the entire plotted spectral region. Almost the entire frequency region depicted in FIG. 1 is accessible with a C-band multisection DBR laser (e.g., of the type commercially available from Agility Communication, Inc.), whereas a single DFB laser is only capable of covering a much narrower spectral region, such as the region indicated by the peak plotted near 6409 $cm^{-1}$ (as indicated by arrow 1 in FIG. 1).

Figure 2:
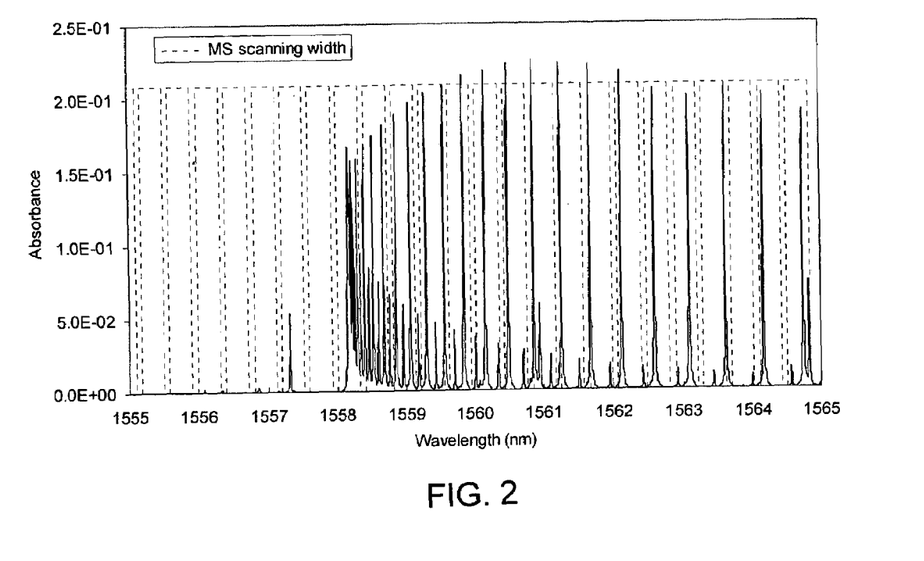
FIG. 2 is an expansion of the absorbance spectra of the plot of FIG. 1 near the CO band head.

In the plot of FIG. 2, an expanded view of the spectral region of FIG. 1 is provided near the CO band head (i.e., between 1555 nm and 1565 nm), and the different ITU-GRID channels that are accessible with the multi-section DBR laser are indicated by the dashed line boxes depicted in this figure. The width of each channel or dashed box of FIG. 2 indicates the tuning range of the laser. It is noted that the laser can be refined or tuned to further reduce gaps between the channels as desired for a particular application. As is clearly evident from the data plotted in FIGS. 1 and 2, the multisection DBR laser is capable of scanning many CO absorption transitions, as opposed to the narrow range of spectra that can be obtained by a single DFB laser. This enhances the measurement accuracy of a system employing a multisection DBR laser due to the larger range of spectral features that can be monitored by a single laser.

One or more multisection DBR lasers can be utilized in any gas species detection and monitoring system to facilitate enhanced control and operability of the system based upon providing reliable and accurate detection and concentration information of gas species at various processing locations within the system. As noted above, the selection of a particular multisection DBR laser (e.g., C-band, S-band, O-band, etc.) will be based upon the types of gas species to be monitored at the varying locations or measurement points as well as the temperature and/or other conditions that may influence the absorption spectra at such measuring locations.

Figure 3:
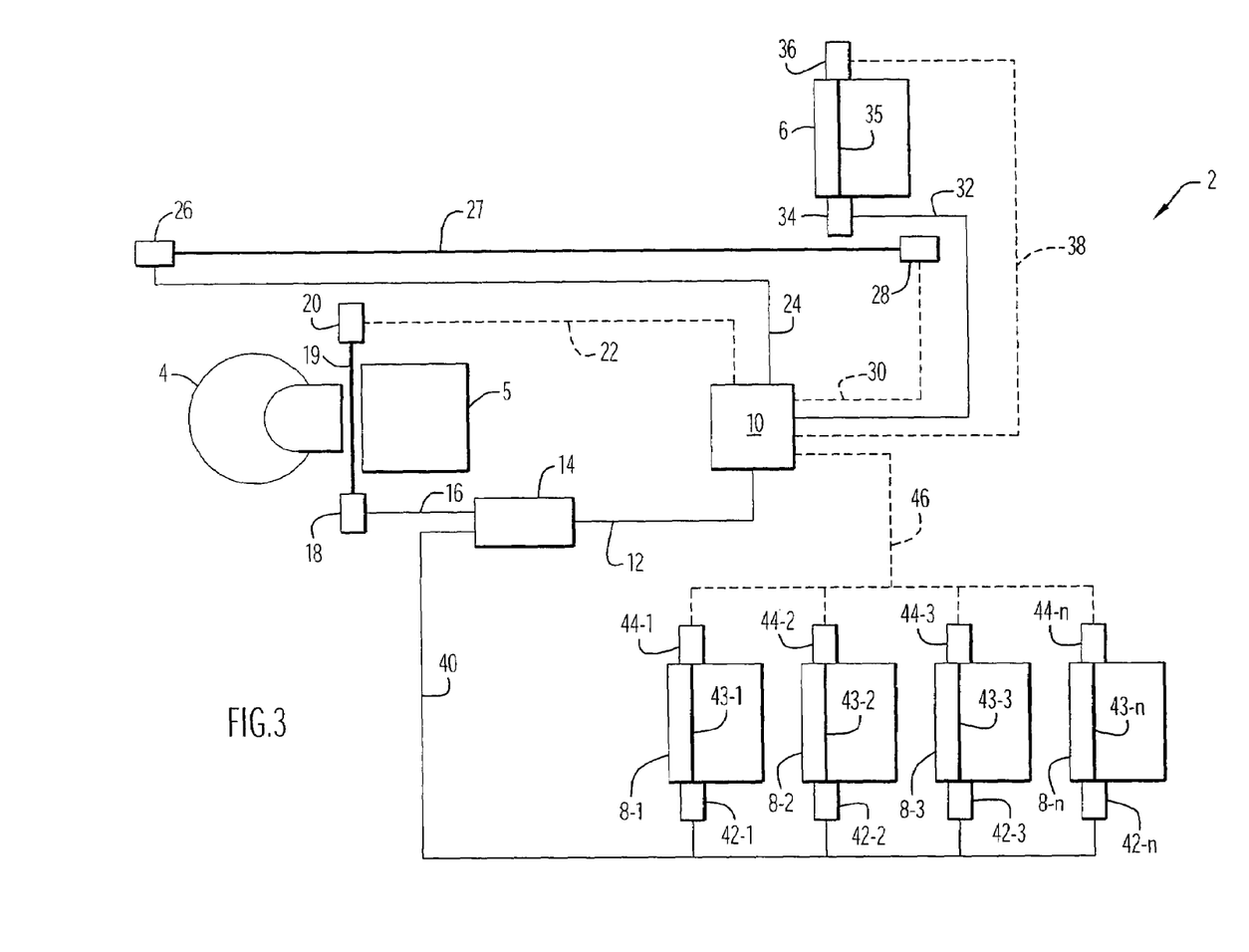
FIG. 3 is a schematic of a system employing a single multisection DBR laser in a laser acquisition/processing system for monitoring gas species in a steel mini-mill in accordance with the present invention.

In an exemplary embodiment of the invention, a gas species detection and monitoring system is implemented in a steel mill as schematically depicted in FIG. 3, where the steel mill includes an electric arc furnace and various other furnaces as well as a laser acquisition and processing system to detect and measure the concentrations of gas species. The laser acquisition/processing system includes a single multisection DBR laser and various fiber optic cables for distributing laser beams to various measurement point locations within the steel mill so as to facilitate gas species monitoring at the various locations.

At each measurement point within the steel mill, a launch module (LM) is provided to receive a laser beam or signal from the laser acquisition/processing system, where the LM includes suitable shaping and collimating optics to collimate the laser beam or signal to a selected diameter and divergence before sending the signal to the respective measurement point. In addition, a receiver module (RM) is provided at every measurement point to receive laser radiation that has been propagated through the measurement point, where the receiver module includes mirrors and/or other suitable optics as well as at least one photodetector to monitor the intensity of the laser beam or signal that is received from the measurement point so as to correlate the intensity with the presence and concentration of gas species within the measurement point. The launch and receiver modules can be of any conventional or other suitable type including, without limitation, those that are described in U.S. patent application Publication No. 2003/0152307, the disclosure of which is incorporated herein by reference in its entirety.

Referring to FIG. 3, steel mill 2 includes an electric arc furnace or EAF 4 including an exhaust duct section 5 for receiving off-gas streams from the EAF (e.g., from the "fourth hole" of the EAF). The steel mill further includes a reheat furnace 6 and a series of heat treating furnaces 8-1, 8-2, . . . , 8-n that are all used in a conventional and well known manner in steel production. Each of the EAF, reheat furnace and heat treating furnaces may operate at varying temperatures and require monitoring and detection of different gas species to ensure that optimum performance of the furnaces is maintained throughout the steel production process.

A laser acquisition/processing system 10 including a multisection DBR laser as described above provides laser radiation to measurement point locations at each of the furnaces in order to monitor one or more of the same or different gas species at the different locations. The laser acquisition/processing system can be located, e.g., in a control room that is partitioned from the furnaces of the mill. A suitable multisection DBR laser is selected to scan over a wavelength range that encompasses the optimum absorption transitions for the various gas species to be monitored and also based upon the range of temperatures associated with each of the measurement points at the various furnaces.

The laser acquisition/processing system also includes one or more optical switches to facilitate propagation of the laser beam through a selected fiber optic cable that leads to a specific measurement point or location within the system during operation. Alternatively, or in combination with the optical switch or switches, the laser acquisition/processing system can also include any suitable number of 1×n splitters to facilitate selective delivery of split laser signals to two or more measurement points within the steel mill at the same time during system operation. In addition, one or more variable optical attenuators (VOAs) can be provided in the laser acquisition/processing system and/or at any other suitable locations (e.g., after amplification of the laser beam or signal) within the steel mill to attenuate a laser signal to varying levels as desired prior to the laser beam being propagated through a particular measurement point of the steel mill.

Laser acquisition/processing system 10 further includes a suitable processor to process measured signals received from the various receiver modules at measurement points for comparison to a reference signal so as to determine the presence and concentration of particular gas species of interest at such measurement points. In particular, it is noted that, for each laser beam or signal sent to a particular measurement point or location within steel mill 2, a reference signal is also obtained (e.g., by splitting the signal prior to being sent to the measurement point). For ease of illustration, the splitting of the laser signals prior to delivery to a particular launch module has not been shown in FIG. 3. However, it is to be understood that the reference signal can be obtained at any suitable location within the system (e.g., within the laser acquisition/processing system, at a location prior to each launch module, etc.).

The reference signal and the measured signal from the receiver module at the particular measurement point are sent to the processor of the laser acquisition/processing system to facilitate suitable calibration and/or other processing of the signal in a conventional or any other suitable manner. The processor can include a balance ratiometric detector (BRD) or any other suitable reference device to facilitate such calibration of the measured signal prior to performing spectral data analysis of the signal by the processor. An exemplary BRD that is suitable for use in the laser acquisition/processing system is described in U.S. Pat. No. 5,134,276, the disclosure of which is incorporated herein by reference in its entirety. Alternatively, in applications that utilize direct absorption systems not using a reference channel (i.e., measurements that are made relative to the transmitted baseline), a reference signal need not be generated to calibrate and/or process the measured signal from a RM prior to analysis of the spectral data by the processor of the laser acquisition/processing system.

A fiber optic cable 12 is connected between laser acquisition/processing system 10 and an amplification section 14 to facilitate delivery of a laser beam from the multisection DBR laser to the amplification section for amplification to a suitable level prior to delivery to a measurement point at EAF 4 or a measurement point at one of the heat treating furnaces 8-$n$. The amplification section includes an amplifier (e.g., an EDFA) and also a suitable optical switch to facilitate selective delivery of the amplified laser beam from the amplifier to the EAF via fiber optical cable 16 or to one of the heat treating furnaces via fiber optic cable 40. Alternatively, the amplification section can include a 1×2 splitter to split the amplified signal such that a laser beam can be sent to each of the EAF and one of the heat treating furnaces at the same time. In applications where variable power control is desired, a VOA can also be provided after the amplifier to attenuate the amplified laser beam or signal to selected levels.

At the EAF, a launch module 18 and a receiver module 20 are provided and aligned with each other to facilitate propagation of a laser beam 19 between the launch and receiver modules and through exhaust gases passing through a gap between EAF 4 to duct section 5. Launch module 18 is connected to amplifier 14 via a fiber optic cable 16 so as to receive the amplified laser beam from the amplifier. The measured signal from receiver module 20 is sent, via a communication link 22 (e.g., a wireless link, a fiber optic cable or a wired link), to the laser acquisition/processing system for comparison of the measured signal with the reference signal and analysis of the spectral data as described above.

Each of the heat treating furnaces 8-$n$ include a launch module 42-$n$ and a receiver module 44-3 that are suitably aligned with each other at opposing sides of the furnace to facilitate propagation of a laser beam 43-$n$ through the furnace from the LM to the RM. Fiber optical cable 40 is connected to each LM 42-$n$ (e.g., via a suitable 1×n optical switch) to facilitate selective direction of the laser signal to a particular furnace 8-$n$ of interest during system operation. Each RM 44-$n$ is connected, via a suitable communication link 46 (e.g., a wireless link, a fiber optic cable or a wired link), to laser acquisition/processing system 10. Thus, the measured signal from the furnace through which the laser beam or signal has been propagated can be transmitted to the laser acquisition/processing system for processing of the measured signal with the reference signal and analysis of the spectral data as described above.

Reheat furnace 6 includes a launch module 34 and a receiver module 36 that are suitably aligned with each other at opposing sides of the furnace to facilitate propagation of a laser beam 35 through the furnace from the LM to the RM. Launch module 34 of the reheat furnace is connected to laser acquisition/processing system 10 via a fiber optic cable 32 to facilitate delivery of the laser beam or signal to the LM. In addition, a communication link 38 (e.g., a wireless link, a fiber optic cable or a wired link) connects RM 36 with the laser acquisition/processing system to facilitate transmission of a measured signal from the RM of the reheat furnace to the laser acquisition/processing system for processing of the measured signal with the reference signal and analysis of the spectral data as described above.

A launch module 26 and receiver module 28 are also suitably aligned with each other at a selected location within steel mill 2 to facilitate propagation of a laser beam 27 through the ambient environment from the LM to the RM.

A fiber optic cable 24 connects LM 26 with laser acquisition/processing system 10 to facilitate delivery of the laser signal to the RM, while a communication link 30 connects RM 28 with the laser acquisition/processing system to facilitate transmission of a measured signal from the RM of the ambient environment to the laser acquisition/processing system for processing of the measured signal with the reference signal and analysis of the spectral data as described above.

During operation of mill 2, a laser beam or signal is selectively directed to any one of the measurement locations within the mill to detect and monitor a variety of different gas species at varying temperature conditions. For example, the laser beam can be directed from laser acquisition/processing system 10 to LM 18 at EAF 4 so as to monitor the off-gases from the EAF and thus optimize control and performance of the EAF. The compositions of gas species within each heat treating furnace 43-$n$ can also be monitored utilizing the laser acquisition/processing system to control their operation, as can reheat furnace 35 (e.g., to control temperature and atmosphere composition near the billets within the reheat furnace. In addition, the surrounding environment within the mill can be monitored by system 10, via LM 20 and RM 28, so as to ensure safe air quality is maintained within the mill during system operation. The temperatures at different measurement points can vary significantly (e.g., by about 1800° C. or greater when considering two of the measurement points with the greatest temperature difference, namely, the EAF exhaust location and the ambient environment). However, a single multisection DBR laser is capable of monitoring one or more gas species at these different locations despite the temperature differences at each location.

The laser acquisition/processing system of steel mill 2 can be configured to consecutively monitor each measurement point or location within a select time period or, alternatively, selectively scan a particular measurement point or location based upon any number of system conditions that may trigger a measurement of gas species concentrations at such location. In addition, as noted above, the laser acquisition/processing system can be configured to monitor two or more measurement points or locations simultaneously.

The laser acquisition/processing system further processes the measured signal received from a RM at a particular location by comparison with a reference signal utilizing a BRD or other reference system as noted above, and then analyzes the processed signal to identify and measure one or more gas species of interest at that location. Given the known spectral regions at which the various species absorb at a particular temperature (or within a particular temperature range), where the spectral regions are aligned with one or more bands of the ITU-GRID as described above, the laser acquisition/processing system, which utilizes a multisection DBR laser in accordance with the invention, is capable of quickly and accurately determining concentrations of one or more gas species of interest at the multiple measurement points or locations within the steel mill despite the widely varying temperature ranges at the different locations.

Figure 4:
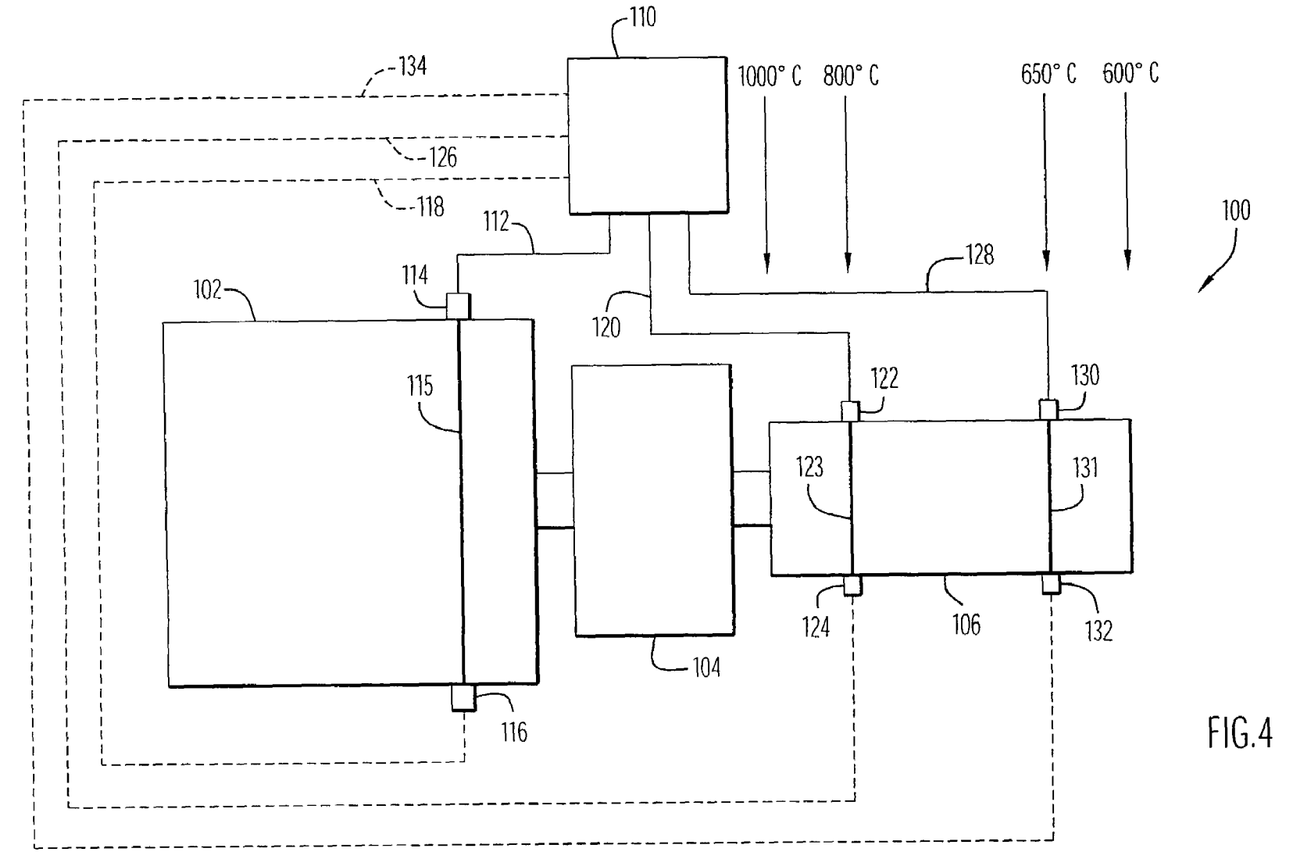
FIG. 4 is a schematic of a system employing a single multisection DBR laser in a laser acquisition/processing system for monitoring gas species in a Float glass furnace in accordance with the present invention.

In another exemplary embodiment of the invention, a gas species detection and monitoring system is implemented in a float glass furnace system 100 as schematically depicted in FIG. 4. System 100 includes a melting section 102 that converts raw materials (e.g., silica, calcium, etc.) into molten glass material at temperatures of about 1400° C. or greater. The molten glass is conditioned in a conditioning zone 104 disposed downstream from the melting section, and then enters a tin bath section 106 for further processing of the glass material. The tin bath section operates at a much lower temperature than the melting section (e.g., at temperatures of between about 600° C. to about 1000° C.). The transition of temperature conditions from the conditioning zone 104 and within tin bath section 106 are further shown by the arrows in FIG. 4. In particular, the temperature of the molten glass material is about 1000° C. when it emerges from the conditioning zone, and the temperature of the glass material continues to decrease at various points as the glass material passes through the tin bath section.

In the float glass system, it is important to monitor concentrations of certain species (e.g., CO) within the melting section to ensure optimization of combustion conditions within this section. In addition, it is very important to monitor conditions of other species within the tin bath section that may be detrimental to the glass forming process (e.g., $H_2O$ content within the tin bath section should not exceed about 300-500 ppm, and is preferably controlled to levels within the range of about 50-100 ppm).

A laser acquisition/processing system 110 is utilized to monitor concentrations of different gas species at a measurement point within melting section 102 and also at different points within tin bath section 106. The laser acquisition/processing system is similar in design and operation to the previously described laser acquisition/processing system for the steel mill system described above and depicted in FIG. 3 and includes the following: a single multisection DBR laser, one or more suitable optical switches and/or splitters to selectively direct a laser beam or signal to one or more measurement points and to generate reference signals, a processor including a BRD or other reference system to calibrate and/or process a measured signal received from a measurement point in order to determine the concentration of one or more gas species at such measurement point, and optional amplifiers and/or VOAs of a conventional or other suitable type to provide a laser signal at the desired power level to a particular measurement point.

At melting section 102, a launch module 114 and a receiver module 116 are provided and aligned with each other to facilitate propagation of a laser beam 115 between the launch and receiver modules and through a refining section of the melting section. Launch module 114 is connected to laser acquisition/processing system 110 via a fiber optic cable 112 so as to facilitate delivery of the laser beam to the LM. The measured signal from receiver module 116 is sent, via a communication link 118 (e.g., a wireless link, a fiber optic cable or a wired link), to the laser acquisition/processing system for comparison of the measured signal with the reference signal and analysis of the spectral data.

Two different measurement points or locations are monitored within the tin bath section, where the temperature at each section varies significantly. In particular, a launch module 122 and a receiver module 124 are provided and aligned with each other to facilitate propagation of a laser beam 123 between the launch and receiver modules and through a first section of tin bath section 106, where the temperature at this section is about 800° C. Launch module 122 is connected to laser acquisition/processing system 110 via a fiber optic cable 120 so as to facilitate delivery of the laser beam to the LM. The measured signal from receiver module 124 is sent, via a communication link 126 (e.g., a wireless link, a fiber optic cable or a wired link), to the laser acquisition/processing system for comparison of the measured signal with the reference signal and analysis of the spectral data.

Another launch module 122 and receiver module 124 are also provided and aligned with each other at a second section of tin bath section 106 to facilitate propagation of a laser beam 131 between the launch and receiver modules and through the second section, where the temperature at this section is about 650° C. Launch module 130 is connected to laser acquisition/processing system 110 via a fiber optic cable 128, while the measured signal from receiver module 132 is sent, via a communication link 134 (e.g., a wireless link, a fiber optic cable or a wired link).

In operation, laser acquisition/processing system 110 selectively delivers a laser beam or signal to one of the launch modules of the melting section or tin bath section. As in the previous embodiment, the laser acquisition/processing system can also be configured to send laser signals to two or more launch modules at the same time. The measured signal received from a particular receiver module is transmitted to the laser acquisition/processing system for processing and determination of the concentration of one or more gas species of interest. As noted above, the temperature variations at different measurement points within the float glass system vary significantly (e.g., the temperature difference can be from about 600° C. to about 800° C. or greater between two or more measurement points). However, the system design, utilizing a single multisection DBR laser, is capable of monitoring different gas species at the widely varying temperature conditions while maintaining speed, accuracy and reliability.

The invention is not limited to the exemplary systems described above. Rather, the chemical detection and monitoring system employing a multisection DBR laser could be used to monitor different measurement points at varying temperature conditions and that are disposed at any suitable locations within a gas-flow system to facilitate an in-situ or ex-situ process analysis and measurement of a gas flowing through the system at the measurement point. By way of non-limiting example, the chemical detection and monitoring system can be utilized to detect any one or more gas species at measurement points or locations that are situated within a particular system to monitor any of the following: a gas near or in the primary combustion chamber of a waste incinerator exhaust duct, a gas at any selected monitoring location in a coal-fired boiler or recovery boiler, the off-gas from a secondary aluminum rotary or reverberatory furnace, the gas of a basic oxygen furnace (BOF), blast furnace gases, etc., where the measurement can be enhanced by increasing and/or controlling the laser power, and a sample cell or external measurement zone that receives an extracted process gas from a selected location within the system for analysis and measurement of gas species.

Thus, the system of the present invention facilitates gas species monitoring at multiple locations utilizing a single multisection laser. As noted above, using individual DFB lasers that are used to access channels of limited wavelength tuning range requires the need for multiplexed lasers for multiple absorption line monitoring. In contrast, by implementing a multi-section laser developed for ITU-GRID communication applications and adapted for gas sensing applications allows for multiple absorption line detection using a single device, thereby simplifying the overall gas sensor system architecture. This in turn facilitates improved monitoring capabilities with regard to measurement accuracy and flexibility. The added flexibility provides optimum absorption transition selection that extends the range of conditions (e.g., temperature and concentration) for process monitoring. Thus, the present invention provides a system that distributes light from a single multisection laser to multiple measurement points or locations within a single process and/or throughout a plant.

Having described novel systems and methods for chemical species detection including a multisection laser for improved process monitoring, it is believed that other modifications, variations and changes will be suggested to those skilled in the art in view of the teachings set forth herein. It is therefore to be understood that all such variations, modifications and changes are believed to fall within the scope of the present invention as defined by the appended claims.

The invention claimed is:

1. A gas species monitoring system comprising:
    a laser system comprising a multisection DBR laser; and
    a plurality of measurement points disposed at different locations within the system;
    wherein the laser system is configured to selectively deliver a laser beam from the multisection DBR laser to each measurement point within the gas species monitoring system to determine a concentration of at least one gas species at each measurement point, wherein the temperature difference between the at least two measurement points is at least about 600° C.

2. A method of monitoring one or more gas species at one or more measurement points, comprising:
    directing a laser beam from a multisection DBR laser to a first measurement point to facilitate a measurement of at least one gas species at the first measurement point; and
    directing a laser beam from the multisection DBR laser to a second measurement point to facilitate a measurement of at least one gas species at the second measurement point,
    wherein at least one of a temperature and a gas species differs at each of the first and second measurement points, wherein the temperature difference between the first and second measurement points is at least about 600° C.

* * * * *